US010286095B2

(12) United States Patent
Olson

(10) Patent No.: US 10,286,095 B2
(45) Date of Patent: May 14, 2019

(54) TRAVEL KIT

(71) Applicant: Olson IP Technologies, Inc., Mundelein, IL (US)

(72) Inventor: Richard Carl Olson, Mundelein, IL (US)

(73) Assignee: Olson IP Technologies, Inc., Mundelein, IL (US)

( * ) Notice: Subject to any disclaimer, the term of this patent is extended or adjusted under 35 U.S.C. 154(b) by 138 days.

(21) Appl. No.: 15/261,247

(22) Filed: Sep. 9, 2016

(65) Prior Publication Data

US 2017/0071303 A1 Mar. 16, 2017

Related U.S. Application Data

(60) Provisional application No. 62/217,664, filed on Sep. 11, 2015.

(51) Int. Cl.
*A45C 11/00* (2006.01)
*A61L 2/18* (2006.01)
*A47L 25/00* (2006.01)
*B08B 1/00* (2006.01)

(52) U.S. Cl.
CPC .............. *A61L 2/18* (2013.01); *A45C 11/008* (2013.01); *A47L 25/00* (2013.01); *A45C 2011/007* (2013.01); *B08B 1/00* (2013.01)

(58) Field of Classification Search
CPC . A45C 11/24; A45C 11/008; A45C 2011/007; A61L 2/18; A61M 21/02; A61M 2021/0016; B08B 1/00; B08B 1/006; B65D 71/00; B65D 85/00; A47L 25/00

USPC ................... 206/223, 229, 233, 581; 220/524
See application file for complete search history.

(56) References Cited

U.S. PATENT DOCUMENTS

| | | | | |
|---|---|---|---|---|
| 3,343,540 A | * | 9/1967 | Siegel | A61K 8/22 424/447 |
| 3,487,915 A | * | 1/1970 | Scott | B65D 75/38 206/461 |
| 5,004,106 A | * | 4/1991 | Blumstock | A45C 11/24 206/581 |
| 5,025,920 A | * | 6/1991 | Walsh | A61B 10/0045 206/223 |
| 5,085,208 A | | 2/1992 | Massaro | |
| 5,101,970 A | * | 4/1992 | Turner | A01N 1/00 206/223 |
| 5,111,934 A | * | 5/1992 | Morin | A47K 7/03 206/229 |
| 6,745,895 B2 | * | 6/2004 | Silvers | B65D 1/36 206/233 |
| 7,350,256 B2 | | 4/2008 | Benjamin | |
| 7,820,197 B2 | | 10/2010 | Tsuji | |
| 8,182,826 B2 | | 5/2012 | Whitmire | |

(Continued)

FOREIGN PATENT DOCUMENTS

FR 3004347 10/2014
GB 2419285 4/2006

*Primary Examiner* — Bryon P Gehman
(74) *Attorney, Agent, or Firm* — Fitch, Even, Tabin & Flannery LLP

(57) ABSTRACT

In one aspect, a travel kit is provided for addressing issues a traveler may encounter such as optical, cleanliness, and holistic issues. The travel kit includes a container including a first compartment and a second compartment. There is at least one optical cleaning wipe in the first compartment and at least one disinfectant wipe in the second compartment.

14 Claims, 15 Drawing Sheets

(56) References Cited

U.S. PATENT DOCUMENTS

| | | | |
|---|---|---|---|
| 8,220,625 B2* | 7/2012 | Michaels | A45C 11/24 206/233 |
| 8,337,882 B2 | 12/2012 | Garrow | |
| 8,449,897 B2 | 5/2013 | Whitmire | |
| 8,460,700 B2 | 6/2013 | Singhal | |
| 8,596,458 B1* | 12/2013 | Alcorn | A45C 11/008 206/229 |
| 8,784,903 B2 | 7/2014 | Park | |
| 8,808,757 B2 | 8/2014 | Urschel | |
| 8,846,116 B2 | 9/2014 | Koenig | |
| 8,858,988 B2 | 10/2014 | Chamberland | |
| 9,113,691 B1* | 8/2015 | Picazo | A45D 29/00 |
| 9,540,602 B2* | 1/2017 | Smith, III | A45D 40/24 |
| 2003/0003140 A1 | 1/2003 | Domb | |
| 2003/0012811 A1 | 1/2003 | Paul | |
| 2003/0118528 A1 | 6/2003 | Walters | |
| 2004/0047930 A1 | 3/2004 | Webbe | |
| 2004/0071757 A1 | 4/2004 | Rolf | |
| 2004/0161454 A1 | 8/2004 | Schink | |
| 2004/0228811 A1 | 11/2004 | Krzysik | |
| 2005/0002974 A1 | 1/2005 | Filbry | |
| 2005/0169973 A1 | 8/2005 | Kim | |
| 2006/0110471 A1 | 5/2006 | Nichols | |
| 2007/0023048 A1 | 2/2007 | Cho | |
| 2007/0098710 A1 | 5/2007 | Karita | |
| 2007/0122460 A1 | 5/2007 | Daily | |
| 2007/0141127 A1 | 6/2007 | Casas-Sanchez | |
| 2007/0224254 A1 | 9/2007 | Yu | |
| 2008/0179332 A1* | 7/2008 | Sanders | B65D 25/22 220/524 |
| 2008/0260806 A1 | 10/2008 | Miller | |
| 2008/0311166 A1 | 12/2008 | Wimer | |
| 2008/0311218 A1 | 12/2008 | Oronsky | |
| 2009/0191249 A1 | 7/2009 | Adelakun | |
| 2010/0158986 A1 | 6/2010 | Vincent | |
| 2011/0086084 A1 | 4/2011 | Koenig | |
| 2011/0086085 A1 | 4/2011 | Wenzel | |
| 2011/0159074 A1 | 6/2011 | Warren | |
| 2011/0250227 A1 | 10/2011 | Elraz | |
| 2011/0272304 A1* | 11/2011 | Wahal | A47L 13/17 206/223 |
| 2011/0300198 A1 | 12/2011 | Nussinovitch | |
| 2012/0017937 A1* | 1/2012 | Sabade | A47L 13/12 206/229 |
| 2012/0128753 A1 | 5/2012 | Villalobos | |
| 2012/0209058 A1 | 8/2012 | Arasi | |
| 2013/0059019 A1 | 3/2013 | Leighton | |
| 2013/0059921 A1 | 3/2013 | Marrot | |
| 2013/0108722 A1 | 5/2013 | Stangler | |
| 2013/0202668 A1 | 8/2013 | Prost | |
| 2013/0266671 A1 | 10/2013 | van Aller | |
| 2013/0280320 A1 | 10/2013 | Mompon | |
| 2014/0308338 A1 | 10/2014 | Nierle | |
| 2015/0017224 A1 | 1/2015 | Stefani | |

\* cited by examiner

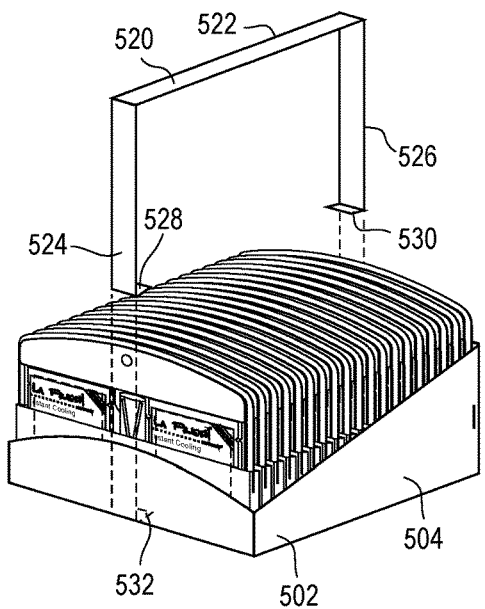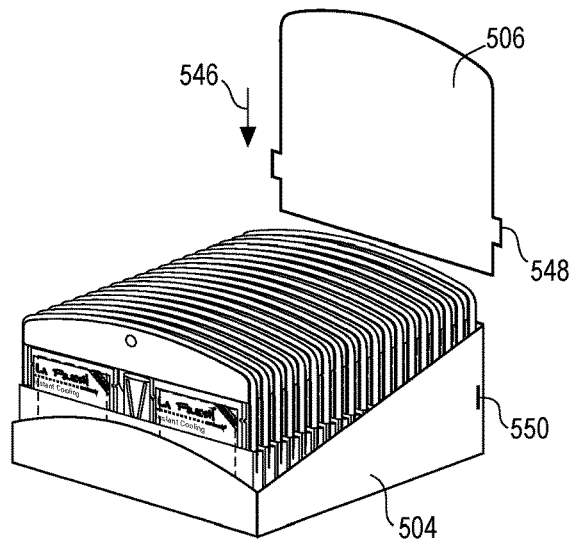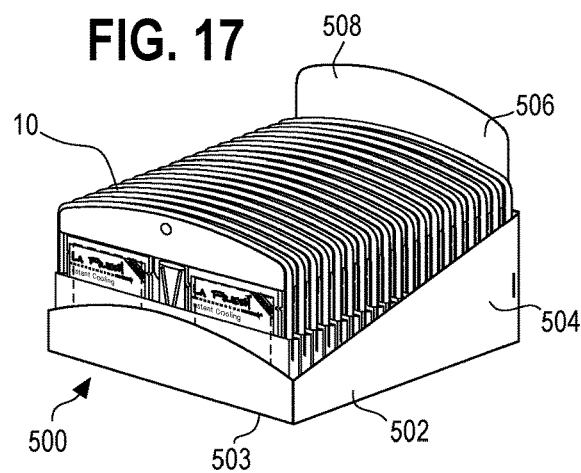

TRAVEL KIT

CROSS-REFERENCE TO RELATED APPLICATION

This application claims the benefit of U.S. Provisional Patent Application No. 62/217,664, filed Sep. 11, 2015, which is hereby incorporated by reference herein.

FIELD

The present disclosure relates to addressing issues encountered while traveling and, more specifically, to packages containing products for addressing these issues.

BACKGROUND

Public travel environments like those in airplanes, trains, buses, automobiles, taxis and ships contain surfaces that a traveler may come into contact with. A traveler may want to disinfect these surfaces to reduce the risk of contracting bacteria and/or viruses from these surfaces. However, it may be difficult for a traveler to obtain cleaning supplies in these environments.

BRIEF DESCRIPTION OF THE DRAWINGS

FIG. 15 is a schematic view of handle being removed from one of the display trays;

FIG. 16 is a schematic view similar to FIG. 15 showing a display board being connected to side walls of the display tray; and FIG. 17 is a schematic view similar to FIG. 16 showing the assembled display tray for displaying the travel kits at point of sale location.

DETAILED DESCRIPTION

In accordance with one aspect of the present disclosure, a travel kit is provided for addressing issues a traveler may encounter such as optical, cleanliness, and holistic issues. The travel kit includes a container having a first compartment and a second compartment. In one form, the travel kit includes an optical cleaning supply in the first compartment, such as at least one optical cleaning wipe, and a cleaning supply in the second compartment, such as at least one disinfectant wipe. The travel kit thereby provides a readily accessible optical cleaning supply for cleaning a surface such as a surface of an eyeglass lens, a window, or a screen of a laptop, tablet, e-reader, or phone. The travel kit further provides a convenient, ready-to-use cleaning supply for disinfecting surfaces in a public transit environment such as in airplanes, trains, buses, automobiles, taxis and ships. In one form, the travel kit includes a third compartment and at least one applicator in the third compartment. The at least one applicator has at least one essential oil. The at least one essential oil may be selected to provide a holistic benefit, such as limiting motion sickness, improving breathing, and/or reducing anxiety.

In accordance with another aspect of the present disclosure, a method is provided for utilizing a travel kit. The method includes opening a container of the travel kit, removing an optical cleaning wipe from the container, and using the optical cleaning wipe to clean a surface. The surface may be, for example, an eyeglass lens, a window, or a screen of a laptop, tablet, e-reader, or phone. The method further includes removing a disinfectant wipe from the container and using the disinfectant wipe to disinfect a surface. The surface may be a surface of an airplane tray table, an airplane arm rest, and/or a seat on a train as some examples. The surface may also be a surface of skin, such as a surface of a hand.

Figure 1:
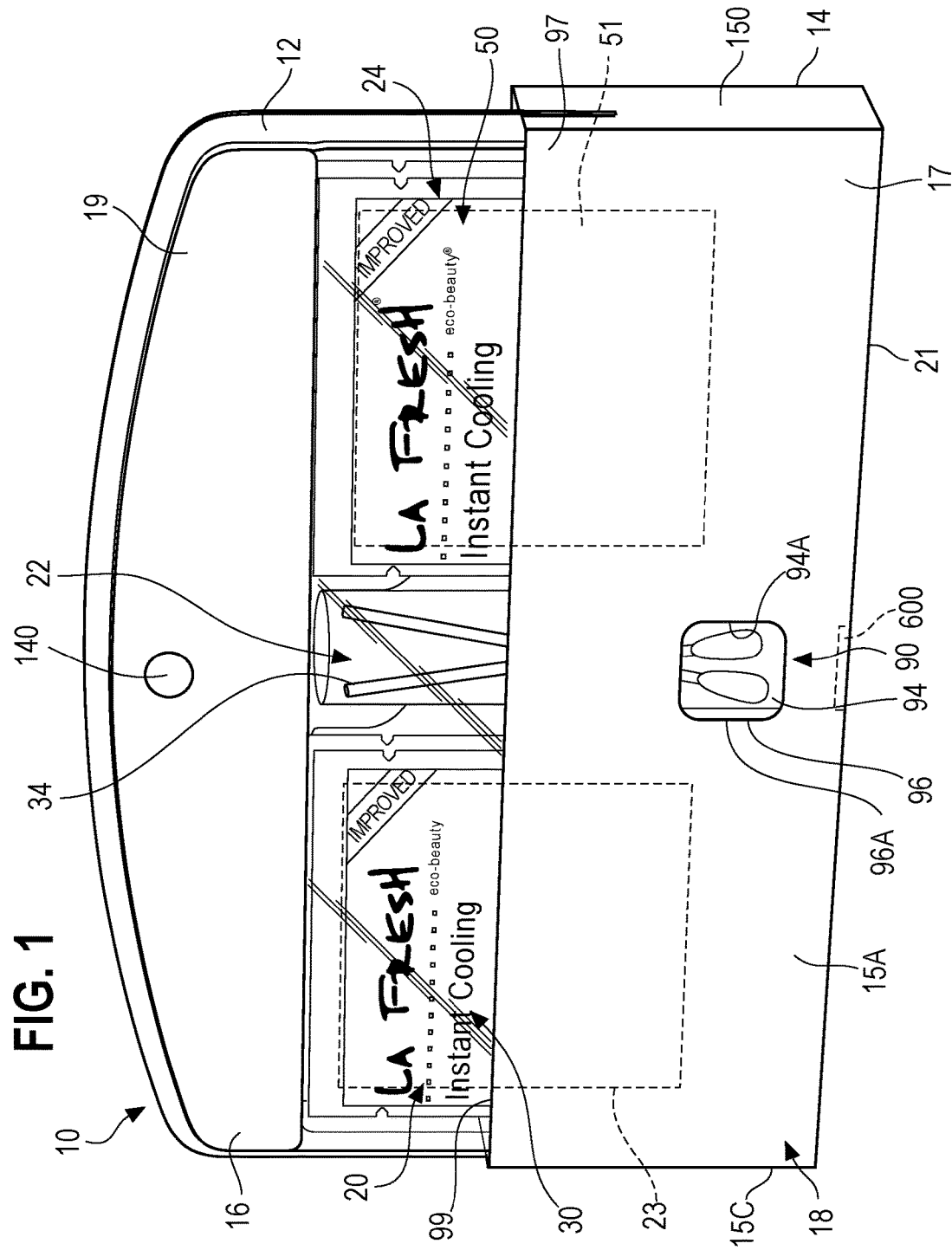
FIG. 1 is a perspective view of a travel kit including a container having three compartments and a sleeve for maintaining the container in an upright configuration.
Figure 5:
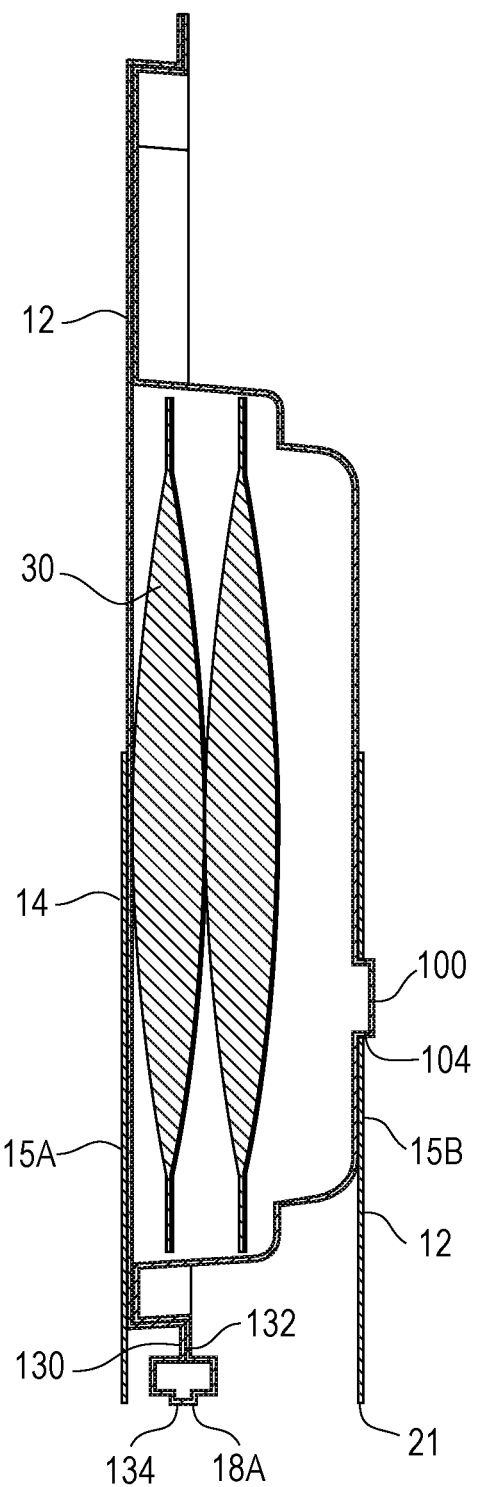
FIG. 5 is a cross-sectional view taken across line 5-5 in FIG. 4 showing a lower edge of the sleeve level with a lower end of the container.

With reference to FIG. 1, a travel kit 10 is provided including a container 12 and a sleeve 14 connected to the container 12. The container 12 has an upper portion 16 and a lower portion 18. The sleeve 14 is connected to the container 12 to maintain the container 12 in an upright orientation with the upper portion 16 above the lower portion 18. The container 12 may be a clam-shell-type container and may be made of a transparent material, such as plastic. The sleeve 14 includes walls 15A, 15B, 15C, 15D extending about the lower portion 18 of the container 12 and having edges 21 for resting on a surface such as a shelf or a floor wall 503 of a display tray 500 (see FIG. 17). The sleeve 14 provides a stable base for the travel kit 10 without having to form a wide base into the clam-shell container itself. With respect to FIG. 5, the edges 21 of the sleeve 14 may be level with a lowermost end 18A of the container 12 so that the edges 21 and the lowermost end 18A together contact the surface (such as floor wall 503) to support the travel kit 10. In another form, the lowermost end 18A may be above the edges 21 so that only the edges 21 support the travel kit 10. Another advantage of the sleeve 14 is that the sleeve provides area 17 for information regarding the travel kit 10 in addition to an area 19 of the travel kit 10.

Figure 2:
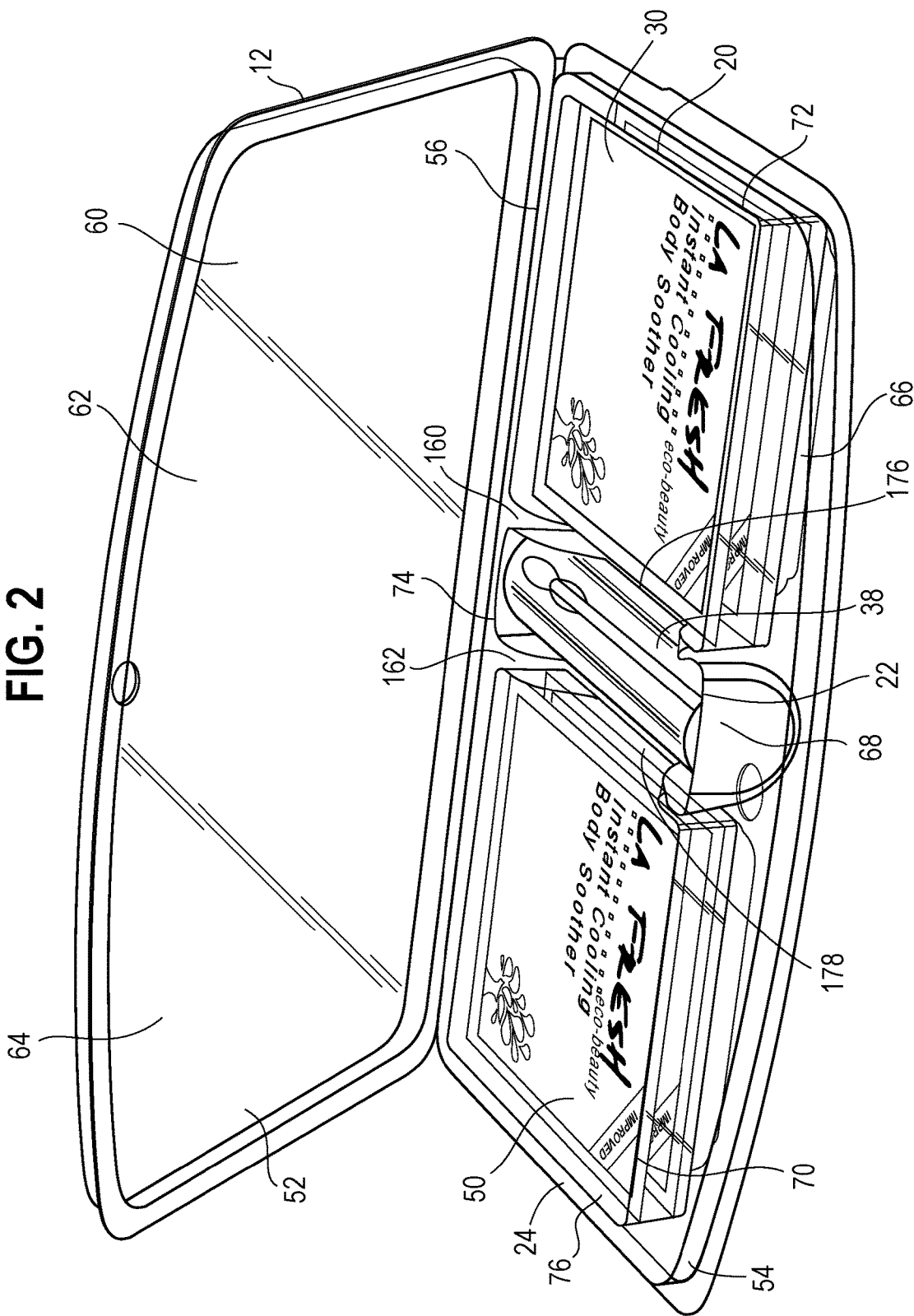
FIG. 2 is a perspective view of the container of FIG. 1 showing the sleeve removed from the container and a lid of the container in an open position.

With respect to FIGS. 1 and 2, the container 12 includes one or more compartments, such as compartments 20, 22, 24. After purchasing the travel kit 10, a user may remove the sleeve 14 to provide access to the compartments 20, 22, 24 and the contents therein. The compartment 20 contains at least one cleaning supply, such as one or more disinfectant wipes 23. In one form, the compartment 20 includes one or more pouches 30 that each contain one or more disinfectant wipes 23. The pouches 30 may be hermetically sealed. In one form, the compartment 20 includes two or more hermetically sealed pouches that each contain one disinfectant wipe 23.

Figure 3:
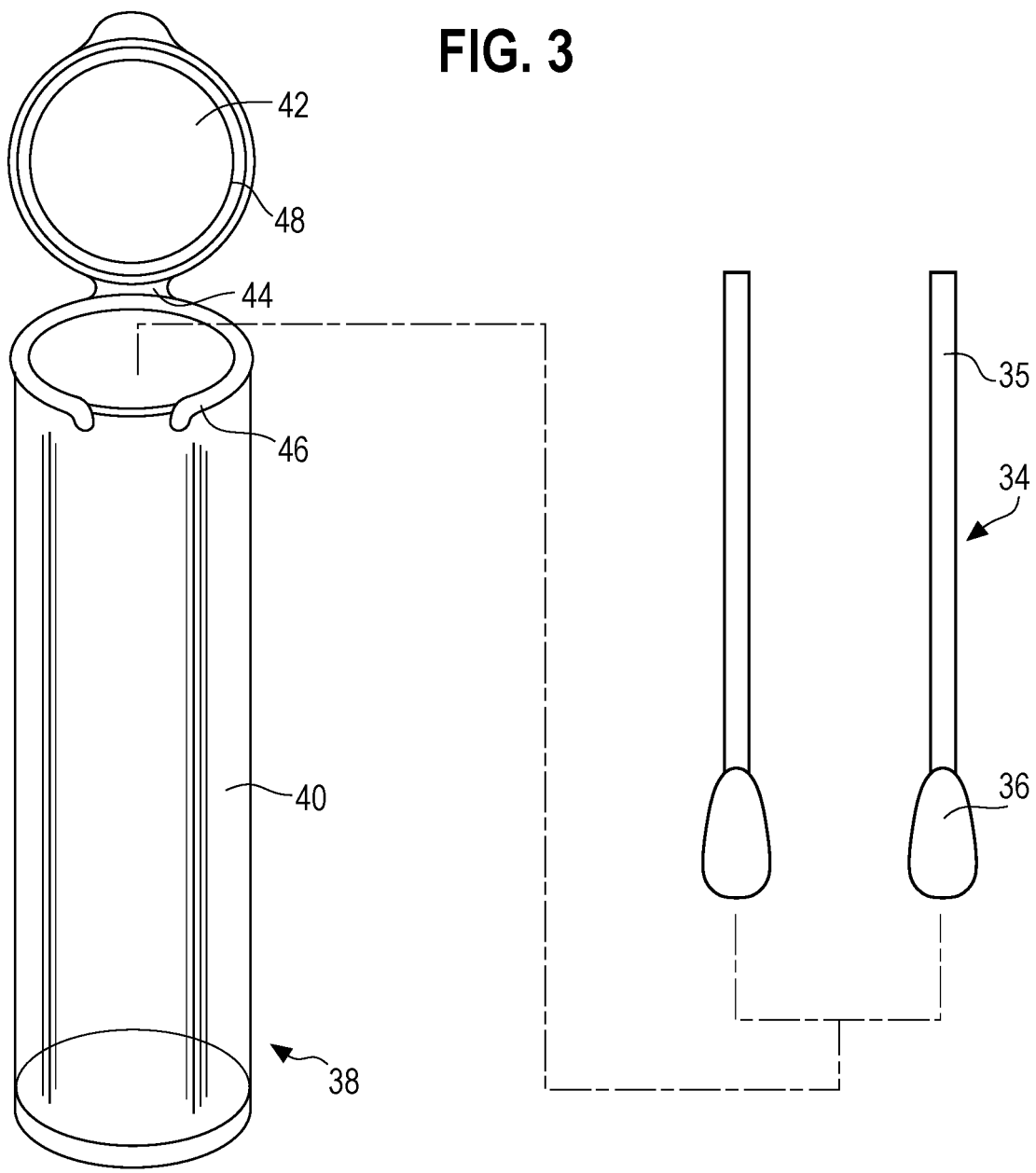
FIG. 3 is a schematic view of a vial contained in one of the compartments of the container of FIG. 2 and cotton swabs that are stored in the vial.

The compartment 22 may contain one or more holistic supplies, such as at least one applicator having an essential oil. For example, the applicator may be one or more cotton swabs 34. With reference to FIG. 3, each cotton swab 34 includes a stick 35 and cotton 36 connected to the stick 35. The one or more cotton swabs 34 may be contained in a vial 38 received in the compartment 22, as shown in FIG. 3. The vial 38 includes a body 40 and a lid 42 connected to the body 40 by a hinge 44. The vial 38 may be airtight so that the essential oils of the cotton 36 do not dry out. Further, the vial 38 may be operated with one hand, such as by a user holding the body 40 in the palm of her hand and using her thumb to remove the lid 42 off of the body 40. Removing the lid 42 from the body 40 permits the lid 42 to pivot upwardly about the hinge 44. In one example, the vial 38 is made of plastic and the body 40, lid 42, and hinge 44 may be monolithically formed.

Returning to FIG. 1, the compartment 24 includes at least one cleaning supply, such as one or more optical cleaning wipes. In one form, the compartment 24 includes one or more pouches 50 that each contain one or more optical cleaning wipes 51. The one or more pouches 50 may be hermetically sealed. In one form, each pouch contains only one optical cleaning wipe 51. The optical cleaning wipes 51 contained in the pouch 50 may be made from a material selected to limit scratching of a surface while removing debris from the surface, such as a surface of an eyeglass lens and/or a screen of an electronic device.

Figure 7:
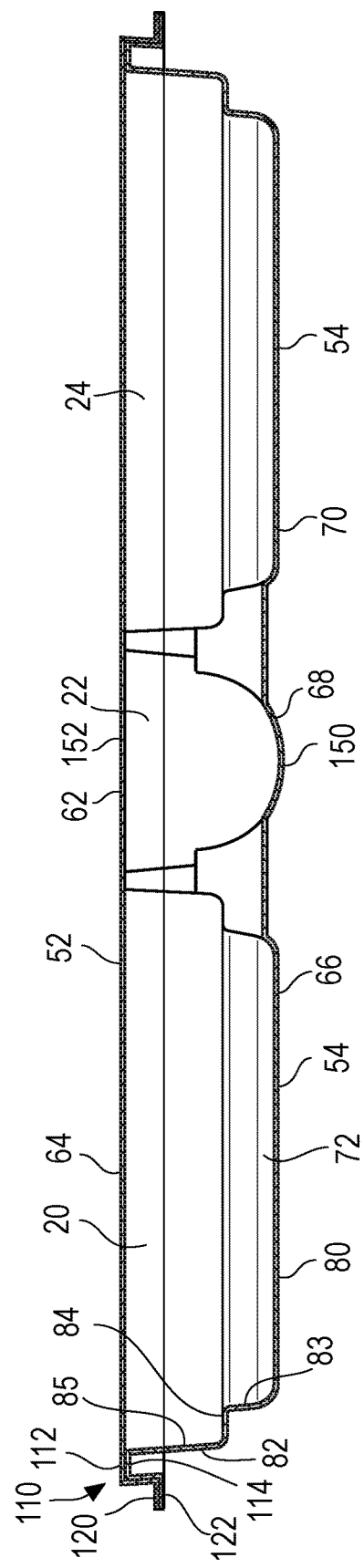
FIG. 7 is a cross-sectional view taken across line 7-7 in FIG. 6 showing cooperating lid and tray portions of the compartments.

With reference to FIG. 2, the container 12 may be a clam-shell-type container having a lid half 52 connected to a tray half 54 by a hinge portion 56. The compartments 20, 22, 24 each include respective lid portions 60, 62, 64 of the lid half 52 and tray portions 66, 68, 70 of the tray half 54. The compartments 20, 22, 24 form cavities 72, 74, 76 that receive the pouches 30, pouches 50, and vial 38. With reference to FIG. 7, the tray portion 66 includes a floor 80 and one or more side walls 82 upstanding from the floor 80 to define at least a portion of the cavity 72. In one approach, the side walls 82 include a first vertical portion 83, a shelf portion 84, and a second vertical portion 85. The shelf portion 84 may support outer portions of the pouches 30, 50. The dimensions of the cavity 72 may be selected to closely conform to the pouch 30 so that the tray portion 66 resists sliding or shifting of the pouch 30 within the compartment 24. In one form, the compartment 24 has a similar configuration as the compartment 20.

Figure 4:
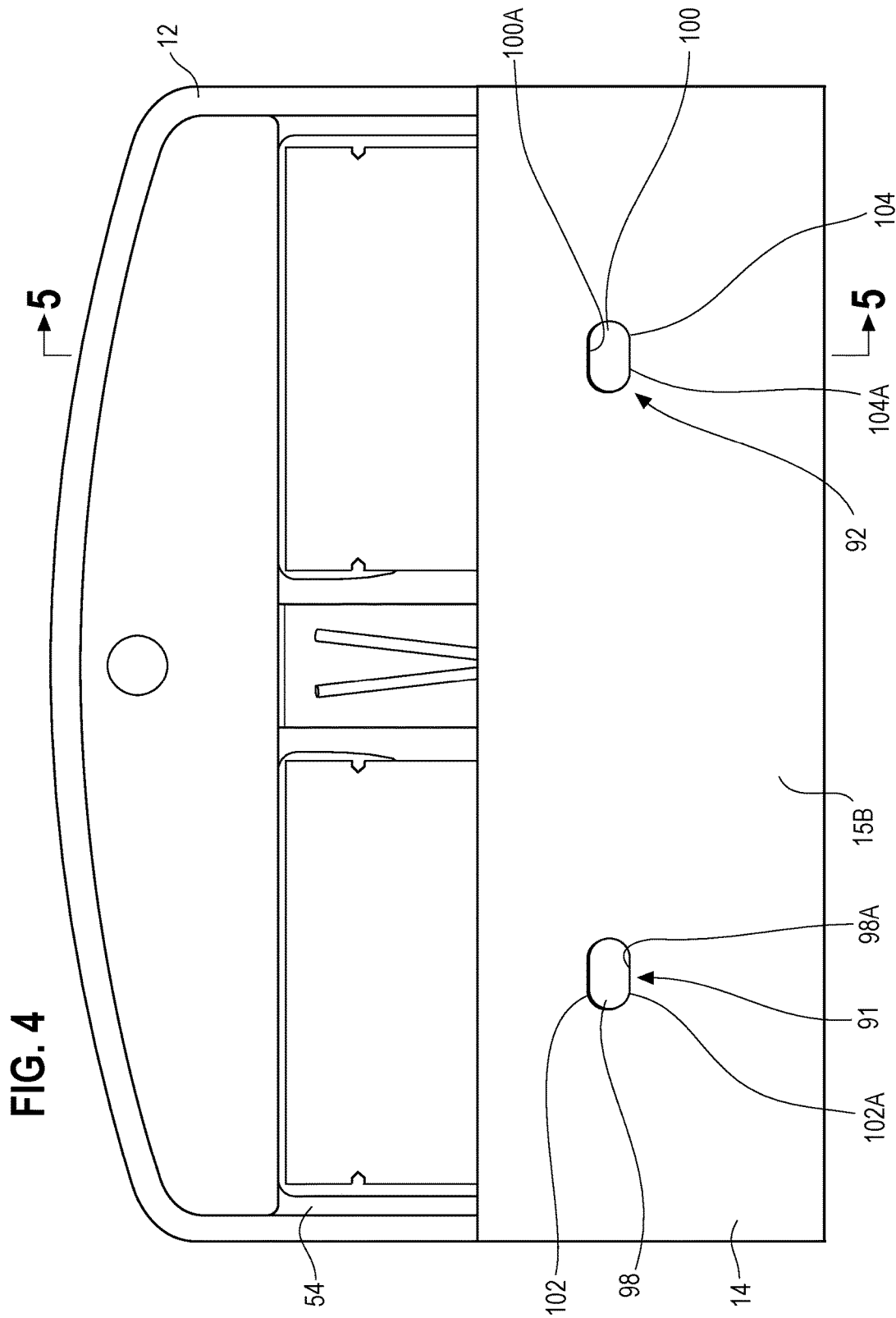
FIG. 4 is a rear elevation view of the travel kit of FIG. 1 showing mating portions of the sleeve and container.

With preference to FIGS. 1 and 4, the sleeve 14 and the container 12 have mating portions 90, 91, 92 that are configured to resist shifting of the sleeve 14 along the container 12. Further, the mating portions 90, 91, 92 keep the sleeve 14 square relative to the container 12 to limit tilting of the area 17 and information thereon relative to the area 19 and information thereon. Limiting tilting of the area 17 provides a more aesthetically pleasing appearance of the areas 17, 19 of the travel kit 10.

In one form, the mating portion 90 includes a protrusion 94 of the lid half 52 extending through an opening 96 of the sleeve 14. The protrusion 94 and the opening 96 may include straight sides 94A and straight edges 96A that abut and limit relative movement therebetween. Further, the protrusion 94 and opening 96 may have a polygonal shape, such as a rectangle, to provide a more positive lock therebetween. The protrusion 94 may be formed with a transparent material to display portions of the cotton swabs 34 to a potential purchaser.

With reference to FIG. 4, the mating portions 91, 92 include a pair of protrusions 98, 100 that extend into openings 102, 104 of the sleeve 14. The protrusions 98, 100 may have straight sides 98A, 100A that abut straight edges 102A, 104A and limit relative movement therebetween. As an example, the protrusions 98, 100 and openings 102, 104 have obround shapes. In other forms, the protrusions 98, 100 and openings 102, 104 may have polygonal shapes as examples.

To disconnect the sleeve 14 from the container 12, a user may pull the walls 15A, 15B of sleeve 14 away from the lid and tray halves 52, 54 to shift the openings 96, 102, 104 off of the protrusions 94, 98, 100. Once the walls openings 96, 102, 104 are clear of the protrusions 94, 98, 100, the user slides the sleeve 14 off of the container 12. In another form, the sleeve 14 may have one or more frangible portions that may be broken to remove the sleeve 14 from the container 12. For example, the sleeve 14 may have a perforated area that can be pulled to form a break in the sleeve 14.

The sleeve 14 may be made from, for example, a paper or a plastic material to provide sufficient support to the container 12 while allowing a user to readily remove the sleeve 14 from the container 12. In one approach, the sleeve 14 is made from a paperboard such as chip board.

With reference to FIG. 7, the lid half 52 includes a skirt 110 having a channel or recess 112 that fits over a rim 114 of the tray half 54. The skirt 110 and the rim 114 may be configured to permit a user to reclose the container 12. For example, the outer dimensions of the rim 114 and the inner dimensions of the skirt 110 may be closely sized to create an interference which maintains the lid and tray halves 52, 54 together. In one form, the skirt 110 and rim 114 may have lugs and recesses configured to interlock and provide a more positive reclose feature.

Figure 6:
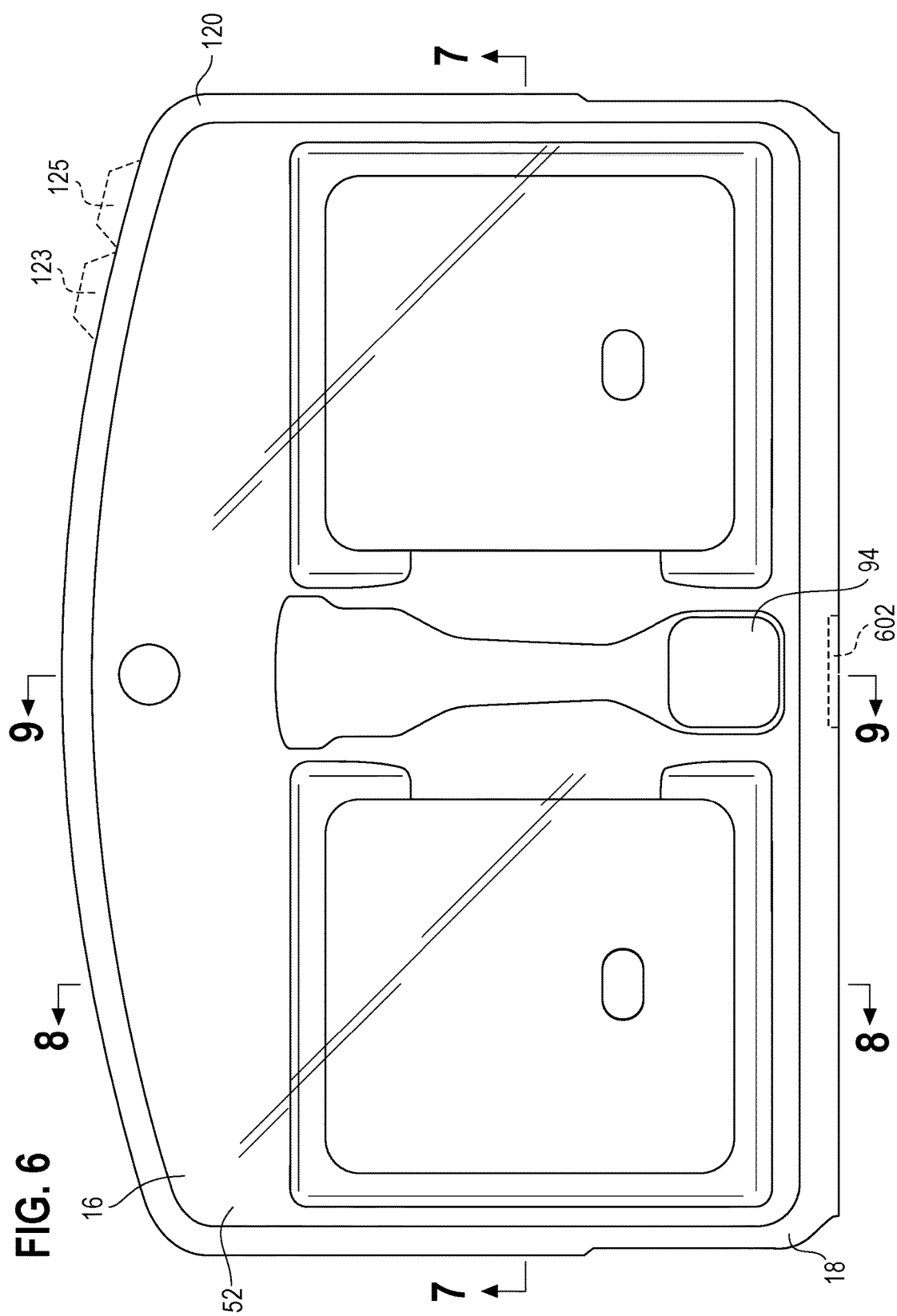
FIG. 6 is a front elevation view of the container of FIG. 1 showing the container by itself.

The lid half 52 and tray half 54 include overlapping peripheral flanges 120, 122 that may be secured together to close the container 12. For example, the peripheral flanges 120, 122 may be secured together by welding or adhesive. In another form, inner portions of the flanges 120, 122 may be secured together while outer portions of the flanges 120, 122 may not be secured together so that a user may grasp the outer portions of the flanges 120, 122 to pull the flanges 120, 122 apart such as by breaking adhesive or welds. With reference to FIG. 6, the flanges 120, 122 may include offset finger tab portions 123, 125 to assist in opening and closing the container 12.

In yet another form, the flanges 120, 122 may not be secured to each other. Instead, the lid and tray halves 52, 54 may include mating lugs and recesses inward of the flanges 120, 122 that interlock and hold the lid and tray halves 52, 54 together. The sleeve 14 may also operate to hold the lid and tray halves 52, 54 together.

Figure 8:
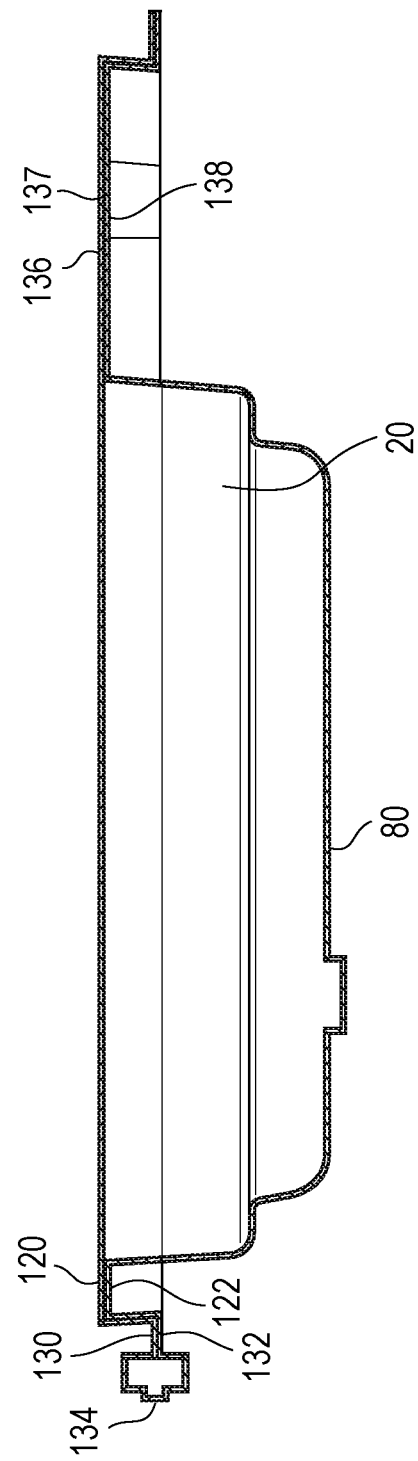
FIG. 8 is a cross-sectional view taken across 8-8 in FIG. 6 showing overlapping flanges of the halves of the container.

With reference to FIG. 8, the lid and tray flanges 120, 122 include lower flange portions 130, 132 that are connected by a hinge portion 134. The hinge portion 134 permits the lid and tray halves 52, 54 to pivot relative to each other during opening and closing of the container 12. At the opposite end of the container 12, the lid and tray flanges 120, 122 include ridge portions 136, 138. The ridge portions 136, 138 may cooperate to provide viewing of the area 19 with information thereon. For example, the ridge portions 136, 138 may be transparent and the travel kit 10 includes a piece of paper 137 positioned between the ridge portions 136, 138 with text and/or graphics thereon. As another example, the ridge portion 136 may be transparent and the ridge portion 138 may have text and/or graphics thereon that are visible through the ridge portion 136. Further, the ridge portions 136, 138 may have a hole 140 therein (see FIG. 1) to receive a display hook. This allows the travel kit 10 to be hung from a display hook at a point-of-sale location.

Figure 9:
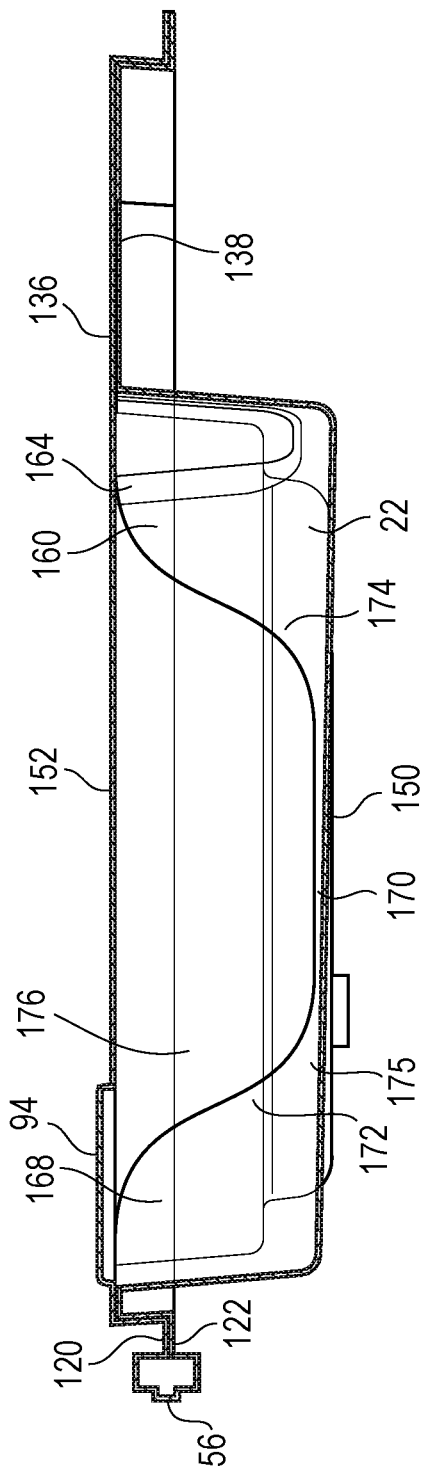
FIG. 9 is a cross-sectional view taken across line 9-9 in FIG. 6 showing the compartment that receives the vial of FIG. 3.

Referring to FIG. 9, a cross-section of the compartment 22 is provided. The compartment 22 includes a tray wall portion 150 and a lid wall portion 152. The protrusion 94 extends outward from the lid wall portion 152 for extending into the opening 96 of the sleeve 14. With reference to FIG. 7, the tray wall portion 150 may be arcuate, and the lid wall portion 152 may be substantially planar. The arcuate tray wall portion 150 may have a curvature matching the outer diameter of the vial 38 to resist side-to-side movement of the vial 38 within the compartment 22.

With reference to FIGS. 2 and 9, the compartment 22 may include walls 160, 162 for separating the contents of the compartment 22 from the contents of the compartments 20 and 24. In one form, the walls 160, 162 have a varying height along their length. For example, the walls 160, 162 may have taller upper and lower portions 164, 168 and a shorter intermediate portion 170 connected to the taller upper and lower portions 164, 168 by tapered portions 174, 175. The varying height of the walls 160, 162 forms openings 176, 178 between the walls 160, 162 and the lid half 52. The openings 176, 178 provide spaces for a user to insert her thumb and fingers onto opposite sides of the vial 38 contained in the compartment 22 to grasp and remove the vial 38 with one hand. Due to the openings 176, 178, the compartments 20, 22, 24 are in communication with each other. In other approaches, the walls 160, 162 may extend to the lid half 52 for their entire length and thereby separate the compartments 20, 22, 24 from each other.

The at least one applicator in the compartment 22, such as the cotton swabs 34, may include one or more essential oils. The one or more essential oils may include ravensara, melaleuca, lemon, peppermint, eucalyptus, tangerine, ylang ylang, sandalwood, lavender, bergamot, ginger-root, jasmine, and coco oil, or combinations thereof. In one form, the essential oils include all of those listed. The cotton swabs 34 include cotton 36 and, in one form, the cotton 36 suspends the essential oils. The cotton swabs 34 also include a stick 35 for handling. The stick 35 may be made from a plastic material, which repels the essential oils and keeps the essential oils suspended in the cotton 36. The essential oils may be applied to the cotton 36 using drops or other techniques.

The cotton swabs 34 may be used to apply the one or more essential oils to her skin. In another approach, the user may inhale the fragrance of the essential oils directly from the cotton 36. In yet another approach, the user may open the vial 38 and leave the cotton swabs 34 within the vial 38. The user may inhale near the open vial 38 from time to time to obtain the benefits of the essential oil(s) when desired. When finished, the cotton swabs 34 may be returned to the vial 38 and the vial 38 may be closed to save the cotton swabs 34 for later use.

The one or more disinfectant wipes 23 may be made from, for example, cotton, paper, and/or nylon. The disinfectant wipes may include alcohol. In another form, the disinfectant wipes 23 utilize natural cleaning solvents and do not include alcohol.

The one or more optical cleaning wipes 51 may be made from, for example, a material containing microfibers. For example, the optical cleaning wipes 51 may be made from a meltblown, fine fiber material.

Figure 10:
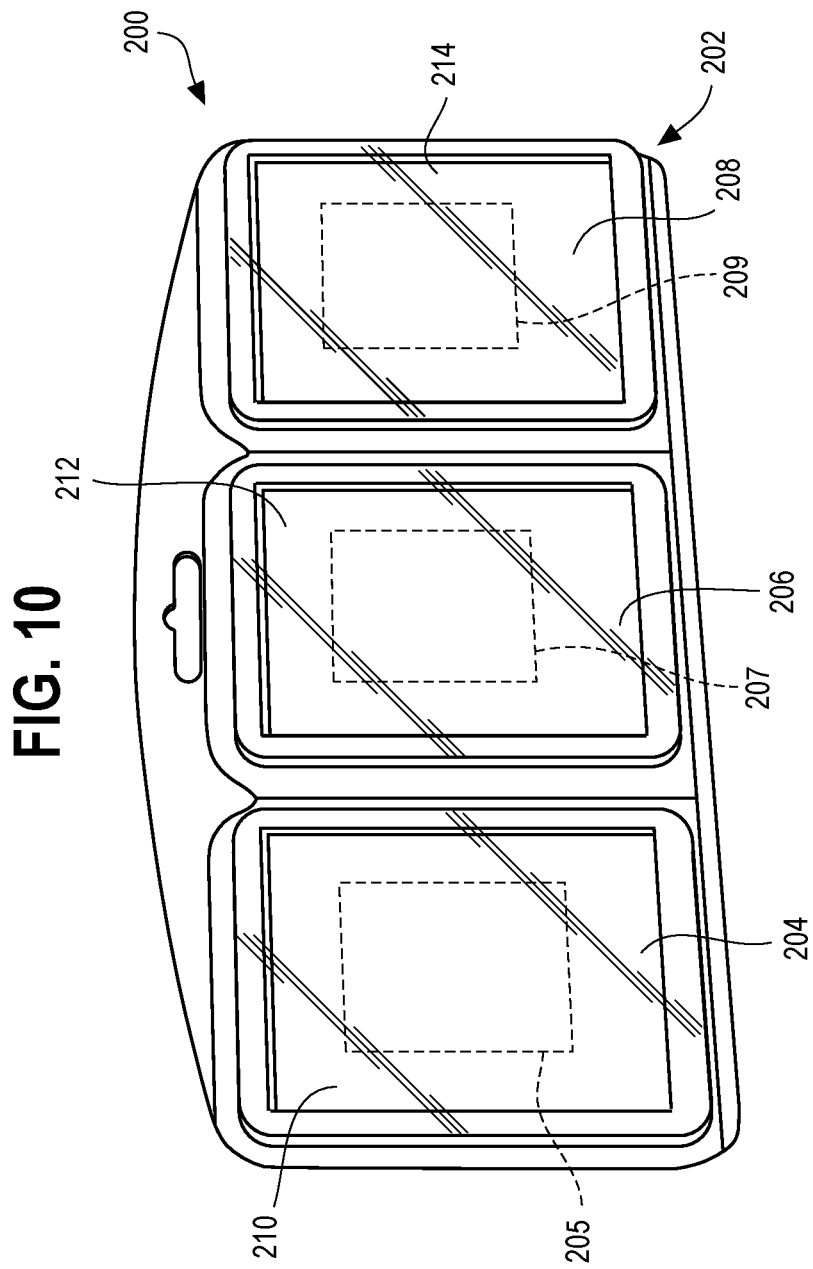
FIG. 10 is a perspective view of another travel kit having three compartments.

With reference to FIG. 10, another travel kit 200 is provided that is similar in many respects to the travel kit 10 such that differences between the two will be discussed. The travel kit 200 includes a container 202 with compartments 204, 206, 208 that include various cleaning supplies. For example, the compartment 204 may include a cleaning supply, such as at least one disinfecting wipe 205. The compartment 206 may include at least one essential oil applicator, such as at least one wipe 207. The container 202 may include an optical cleaning supply, such as at least one optical cleaning wipe 209. In one form, compartments 204, 206, 208 contain pouches 210, 212, 214 that each contain one or more wipes 205, 207, 209.

Figure 11:
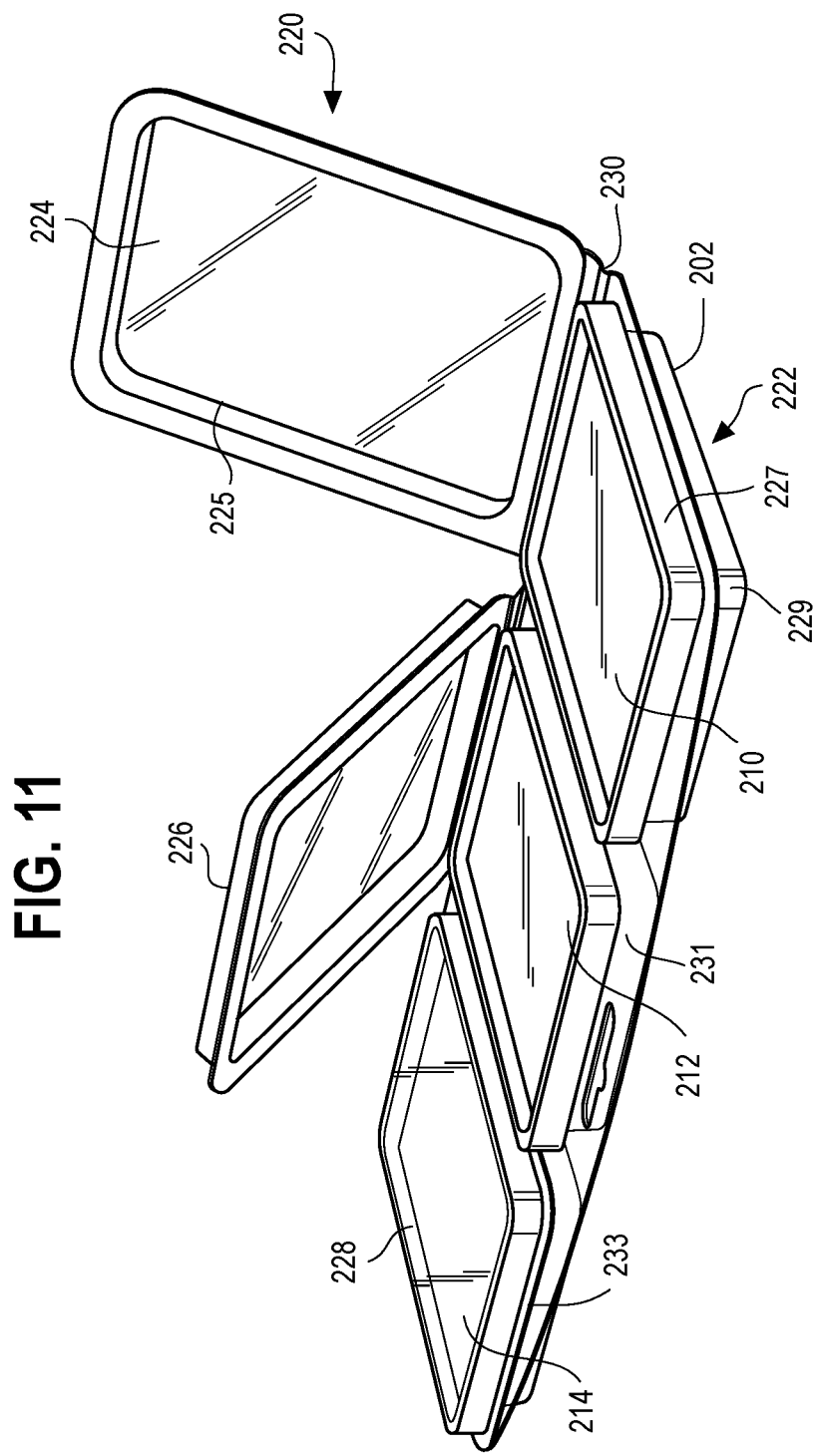
FIG. 11 is a perspective view of the travel kit of FIG. 10 showing lids of the travel kit that are independently operable of one another.

With reference to FIG. 11, the container 202 includes a lid half 220 and a tray half 222. The lid half 220 includes lid portions 224, 226, 228 that are each connected by a respective hinge portions 230 to the tray half 222. In this manner, each of the lid portions 224, 226, 228 may be independently opened and closed to access the pouches 210, 212, 214 contained in the compartments 204, 206, 208.

The compartments 204, 206, 208 may also be reclosable. For example, the lid portions 224, 226, 228 may each include a skirt 225 that snaps onto a rim 227 of the corresponding tray portions 229, 231, 233 of the compartments 204, 206, 208.

Figure 12:
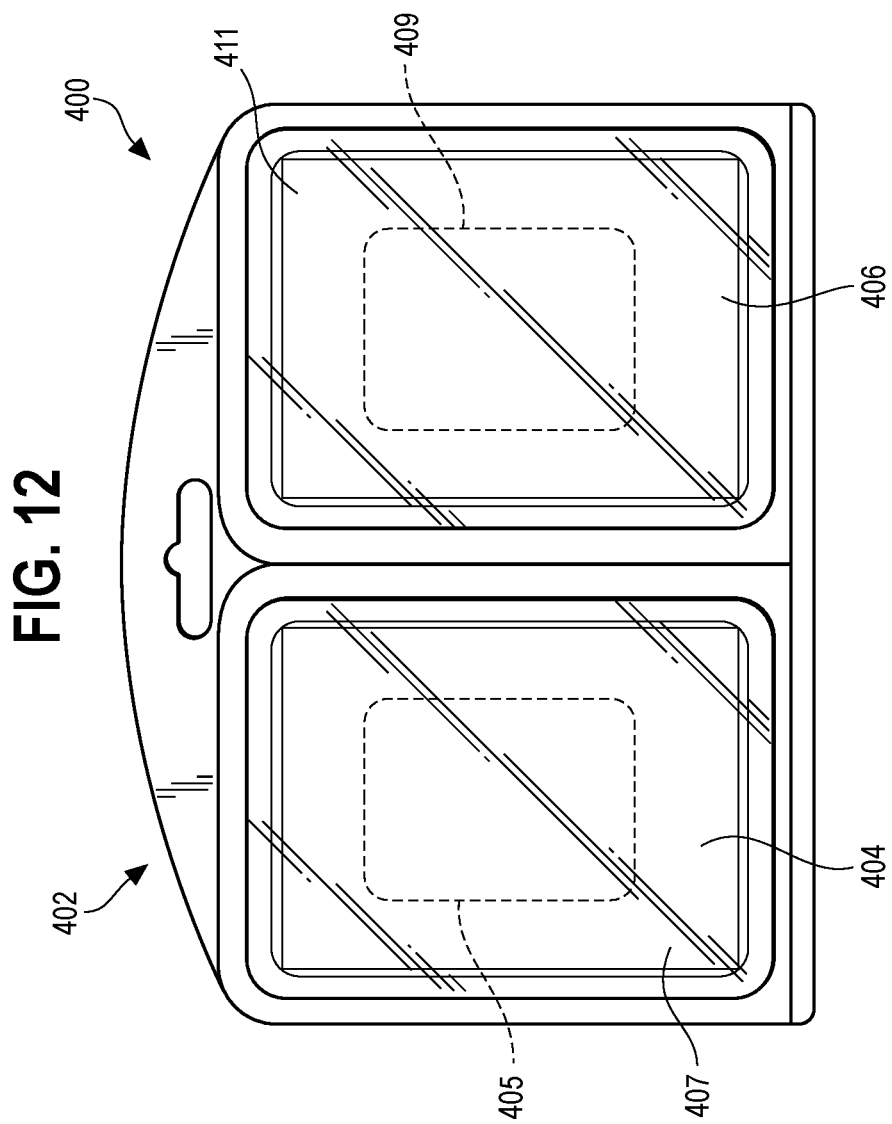
FIG. 12 is a front elevation view of another travel kit having two compartments.
Figure 13:
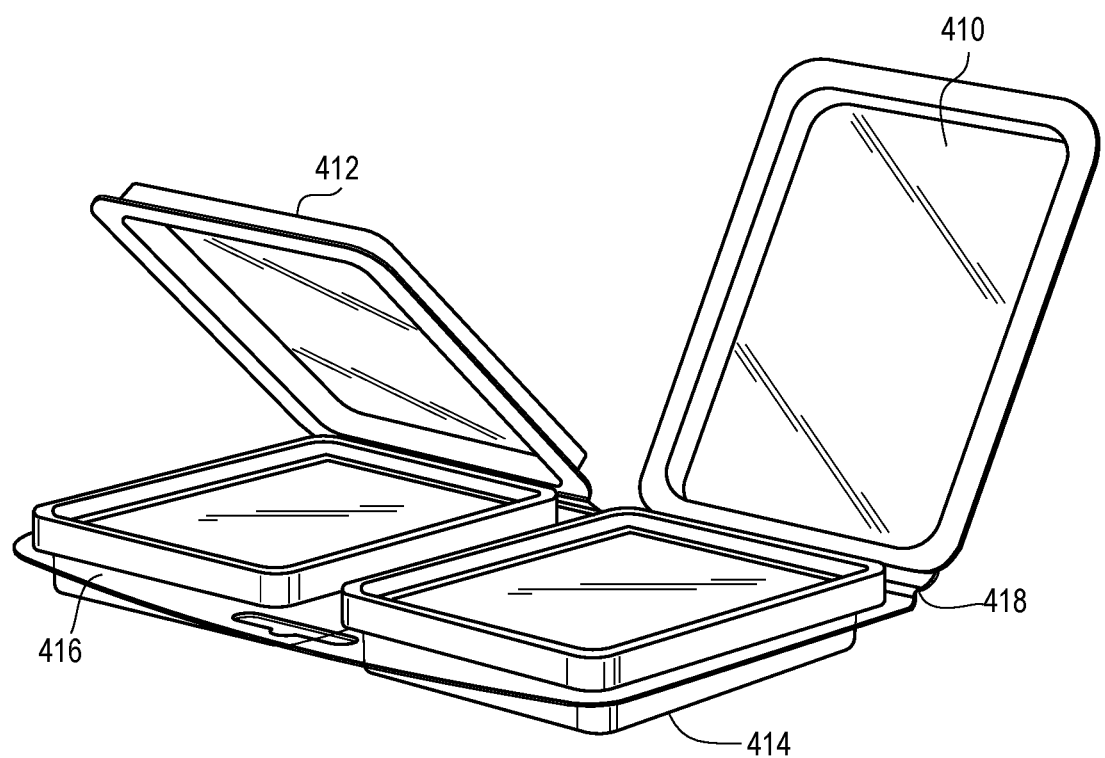
FIG. 13 is a perspective view of the travel kit of FIG. 12 showing the lids of the travel kit that are independently operable of one another.

With reference to FIGS. 12 and 13, another travel kit 400 is provided. The travel kit 400 includes a container 402 having two compartments 404, 406. In one form, the compartment 404 includes a cleaning supply, such as at least one disinfecting wipe 405, which may be provided in at least one pouch 407. The compartment 406 includes at least one optical cleaning supply, such as at least one optical cleaning wipe 409 provided in at least one pouch 411. The compartments 404, 406 include lid portions 410, 412 and tray portions 414, 416. Hinge portions 418 connect the lid portions 410, 412 to the tray portions 414, 416 and permit the lid portions 410, 412 to be opened independently of one another. The compartments 404, 406 may be reclosable.

Moving to FIG. 17, a plurality of travel kits 10 may be provided in a display 500. The display 500 includes a tray 502 with a floor wall 503 and side walls 504 for supporting the travel kits 10 in an ordered configuration, e.g., the travel kits 10 being organized in a single file manner. The display 500 includes a display board 506 that extends vertically higher than the travel kits 10 and includes information 508 which may be readily observed by a potential purchaser. The information 508 may include text and graphics such as a brand name, description of the travel kits, and/or other information. The displays 500 may be provided at a point of sale such as near a cash register or elsewhere within a store, such as in an aisle for travel amenities.

Figure 14:
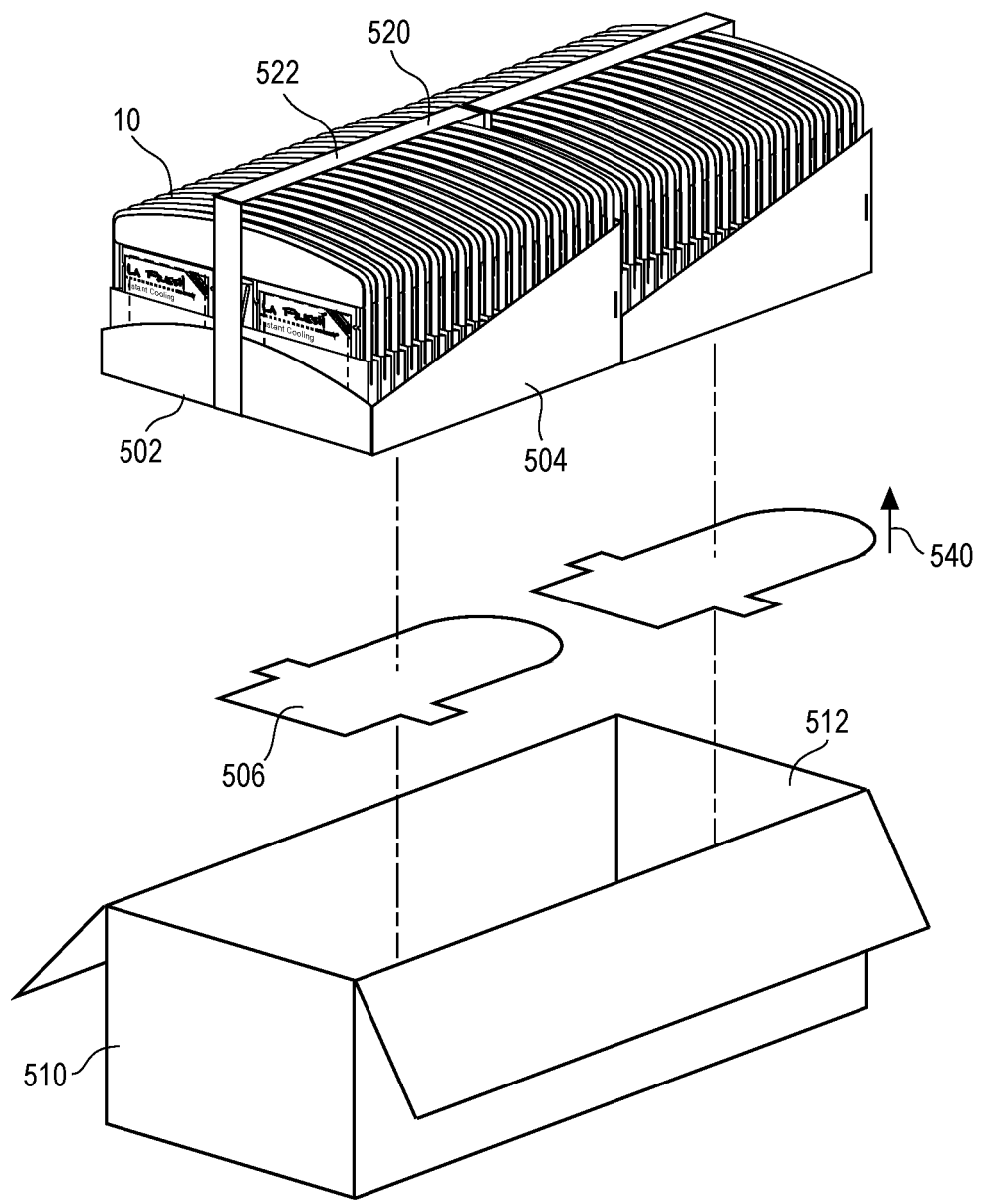
FIG. 14 is a schematic view of travel kits and display trays that are received in a box for transport.

With reference to FIG. 14, two of the displays 500 may be transported, such as from a manufacturer to a reseller, using a case or box 510. The displays 500 may be provided in the box 510 in a partially disassembled configuration. Specifically, the display boards 506 may first be inserted into an interior 512 of the box 510, and the display trays 502 with the travel kits 10 thereon may be inserted into the interior 512 and onto the display boards 506 therein. In one approach, the display trays 502 are connected to removable handles 520 when the display trays 502 are positioned in the interior 512 of the box 510. Turning to FIG. 15, the removable handles 520 include a cross member 522 and legs 524, 526 with tabs 528, 530. The tabs 528, 530 fit into slots 532 of the display tray 502. The handles 520 make it easier to lift the display trays 502 out of the box 510 in direction 540 (see FIG. 14) without having to try to grasp the floor wall 503 or the side walls 504, which may be difficult given the presence of the travel kits 10 and the walls of the box 510. This allows the display tray 502 to be closely sized to match the interior 512 of the box 510. In other words, the display tray 502 does not need to be narrowed to provide space between the display tray 502 and the box 510 for a user grasp the floor wall 503 or the side walls 504.

Once the display tray 502 has been removed from the box 510, the user may pull the tabs 528, 530 outward from the slots 532 and remove the handle 520. The display board 506 may then be connected to the display tray 502 by advancing the display board 506 in direction 546 near the rear side wall 504 of the display tray 502. The display board 506 has tabs 548 for engaging slots 550 of the side walls 504. In this manner, the display tray 502 with travel kits 10 therein may be easily removed from the box 510 and assembled at a retail location.

With reference to FIGS. 1 and 6, the sleeve 14 and the container 12 may include openings, such as notches at areas 600, 602. The wall 15B of the sleeve 14 may include a notched area 600 aligned with the notched area 600 in the wall 15A. The notched areas 600, 602 provide an area to accommodate the tabs 528, 530. In other words, the notched areas 600, 602 permit the front and rear travel kits 10 in the display tray 502 to sit flat on the display tray 502 despite the tabs 528, 530 extending through the slots 532.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of the technological contribution. The actual scope of the protection sought is intended to be defined in the following claims.

What is claimed is:

1. A travel kit comprising:
   a clamshell container including a first compartment a second compartment, and a third compartment;
   at least one optical cleaning wipe in the first compartment;
   at least one disinfectant wipe in the second compartment; and
   at least one applicator in the third compartment, the at least one applicator having at least one essential oil.

2. The travel kit of claim 1 wherein each of the at least one applicator includes a plastic handle and a cotton ball connected to the plastic handle, the cotton ball including the at least one essential oil.

3. The travel kit of claim 1 wherein the clamshell container includes an upper portion and a lower portion; and
   a sleeve connected to the clamshell container and extending about the lower portion of the clamshell container to support the clamshell container in an upright orientation with the upper portion above the lower portion.

4. The travel kit of claim 3 wherein the clamshell container includes a pair of halves connected by a hinge portion with one half having at least one projection and the sleeve includes at least one opening sized to receive the at least one projection of the clamshell container.

5. The travel kit of claim 1 wherein the first compartment includes a first lid portion and a first tray portion and the second compartment includes a second lid portion and a second tray portion, the clamshell container including at least one hinge portion connecting the first and second lid portions to the first and second tray portions.

6. The travel kit of claim 5 wherein the clamshell container has a monolithic construction.

7. The travel kit of claim 6 wherein the monolithic clamshell container is plastic.

8. The travel kit of claim 1 wherein the at least one optical cleaning wipe includes microfibers.

9. The travel kit of claim 1 wherein the at least one disinfectant wipe includes alcohol.

10. The travel kit of claim 1 wherein the at least one essential oil provides a holistic benefit of limiting motion sickness.

11. The travel kit of claim 1 wherein the at least one essential oil provides a holistic benefit of improving breathing.

12. The travel kit of claim 1 wherein the at least one essential oil provides a holistic benefit of reducing anxiety.

13. The travel kit of claim 1 wherein the at least one essential oil is selected from the group consisting of:
    ravensara,
    melaleuca,
    lemon,
    peppermint,
    eucalyptus,
    tangerine,
    ylang ylang,
    sandalwood,
    lavender,
    bergamot,
    ginger-root,
    jasmine,
    coconut oil, or
    combinations thereof.

14. The travel kit of claim 1 wherein the clamshell container includes a pair of halves connected by a hinge portion with each half having a flange; and
    each flange having a through opening aligned with the through opening of the other flange, the aligned openings sized to receive a display hook.

* * * * *